United States Patent [19]
Parker et al.

[11] Patent Number: 5,587,366
[45] Date of Patent: Dec. 24, 1996

[54] COMPOSITIONS USEFUL IN PROPHYLAXIS AND THERAPY OF ENDOTOXIN RELATED CONDITIONS

[75] Inventors: Thomas S. Parker, Brooklyn; Daniel M. Levine, New York, both of N.Y.; Albert L. Rubin, Englewood, N.J.; Bruce R. Gordon; Stuart D. Saal, both of New York, N.Y.

[73] Assignee: The Rogosin Institute, New York, N.Y.

[21] Appl. No.: 487,461

[22] Filed: Jun. 7, 1995

Related U.S. Application Data

[63] Continuation-in-part of Ser. No. 288,568, filed as PCT/US93/07453, Aug. 9, 1993, Pat. No. 5,506,218, which is a continuation-in-part of Ser. No. 928,930, Aug. 12, 1992, Pat. No. 5,344,822.

[51] Int. Cl.$^6$ .................. A61K 31/685; A61K 31/56; A61K 31/22; A61K 31/23; A61K 31/13
[52] U.S. Cl. .................. 514/78; 514/171; 514/549; 514/552; 514/671
[58] Field of Search .................. 514/78, 171, 549, 514/552, 671

[56] References Cited

U.S. PATENT DOCUMENTS

| | | | |
|---|---|---|---|
| 4,818,537 | 4/1989 | Guo | 424/427 |
| 5,376,452 | 12/1994 | Hope et al. | 428/402.2 |

OTHER PUBLICATIONS

Schwarzenberg, et al, "Ursodeoxycholic Acid Modifies Gut-Derived Endotoxemia In Neonatal Rats", Ped. Res. 35(2):214–217 (1994).

Calmus, et al, "Differential Effects of Chenodeoxycholic and Ursodeoxycholic Acids on Interleukin 1, . . ." Hepatology 16(3):719–723 (1992).

Pain, et al, "Prevention of Postoperative renal dysfunction in patients with obstructive jaundice: a multicentre study of bile salts and lactulose", Br. J. Surg. 78:467–469 (1991).

Greve, et al, "Bile Acids Inhibit Endotoxin—Induced Release of Tumor Necrosis Factor By Monocytes: An In Vitro Study", Hepatology 10(4):454–458 (1989).

Cahill, et al, "Bile Salts, Endotoxin And Renal Function In Obstructive Jaundice", Surg. Gynec. & Obstet. 165:519–522 (Dec. 1987).

Thompson, et al, "A randomized clinical trial of oral ursodeoxycholic acid in obstructive jaundice", Br. J. Surg. 73:634:636 (1986).

Hoffman, "Chemistry and Enterohepatic Circulation of Bile Acids", Hepatology 4(5):4S–14S (1984).

Bertok, "Physico–Chemical Defense of Vertebrate Organisms: The Role of Bile Acids in Defense Against Bacterial Endotoxins", Persp. Biol. And Med. 1977:70–75 (Autumn 1977).

Kocsar, et al., "Effect of Bile Acids on the International Absorption of Endotoxin in Rats", J. Bacteriol 100(1):220223 (1969).

Ribi, "Reaction of Endotoxin and Surfactants", J. Bacteriol 92(5):1493–1509 (1966).

Facts and Comparisons, Maz 1992, p. 40.

*Primary Examiner*—Kimberly Jordan
*Attorney, Agent, or Firm*—Felfe & Lynch

[57] ABSTRACT

Treatment and prophylaxis of endotoxin caused toxicity is disclosed. This is accomplished by administering phospholipid containing compositions to the subject. The compositions are protein and peptide free, and may contain triglycerides, or other polar or neutral lipids.

5 Claims, 15 Drawing Sheets

Nonpolar Face

Polar Face
18A

Nonpolar Face

Polar Face
Reverse 18A

Nonpolar Face

Polar Face
des Val¹⁰ 18A

Nonpolar Face

Polar Face
AP

LAP-16

LAP-20

Polar Face
LAP-24

Polar Face
APOA-I CONSENSUS

Polar Face
APOA-IV CONSENSUS

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
( A ) LENGTH: 18 amino acids
( B ) TYPE: amino acid
( D ) TOPOLOGY: linear ( x i ) SEQUENCE DESCRIPTION: SEQ ID NO: 1:

Asp Trp Leu Lys Ala Phe Tyr Asp Lys Val Ala Glu Lys Leu Lys
                 5                   10                  15
Glu Ala Phe ( 2 ) INFORMATION FOR SEQ ID NO: 2:

( i ) SEQUENCE CHARACTERISTICS:
( A ) LENGTH: 18 amino acids
( B ) TYPE: amino acid
( D ) TOPOLOGY: linear ( x i ) SEQUENCE DESCRIPTION: SEQ ID NO: 2:

Lys Trp Leu Asp Ala Phe Tyr Lys Asp Val Ala Lys Glu Leu Glu
                 5                   10                  15
Lys Ala Phe (2) INFORMATION FOR SEQ ID NO: 3:

(i) SEQUENCE CHARACTERISTICS:
        (A) LENGTH: 17 amino acids
        (B) TYPE: amino acid
        (D) TOPOLOGY: linear (xi) SEQUENCE DESCRIPTION: SEQ ID NO: 3:

```
Asp  Trp  Leu  Lys  Ala  Phe  Tyr  Asp  Lys  Ala  Glu  Lys  Leu  Lys  Glu
                    5                        10                           15
Ala  Phe
```

(2) INFORMATION FOR SEQ ID NO: 4:

(i) SEQUENCE CHARACTERISTICS:
        (A) LENGTH: 22 amino acids
        (B) TYPE: amino acid
        (D) TOPOLOGY: linear (xi) SEQUENCE DESCRIPTION: SEQ ID NO: 4:

```
Pro  Lys  Leu  Glu  Glu  Leu  Lys  Glu  Lys  Leu  Lys  Glu  Leu  Leu  Glu
                    5                        10                           15
Lys  Leu  Lys  Glu  Lys  Leu  Ala
                    20
```

(2) INFORMATION FOR SEQ ID NO: 5:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO: 5:

```
Val  Ser  Ser  Leu  Lys  Glu  Tyr  Trp  Ser  Ser  Leu  Lys  Glu  Ser  Phe
                    5                        10                           15
Ser
```

(2) INFORMATION FOR SEQ ID NO: 6:

(i) SEQUENCE CHARACTERISTICS:
        (A) LENGTH: 20 amino acids
        (B) TYPE: amino acid
        (D) TOPOLOGY: linear (xi) SEQUENCE DESCRIPTION: SEQ ID NO: 6:

```
Val  Ser  Ser  Leu  Leu  Ser  Ser  Leu  Lys  Glu  Tyr  Trp  Ser  Ser  Leu
                    5                        10                           15
Lys  Glu  Ser  Leu  Ser
                    20
```

(2) INFORMATION FOR SEQ ID NO: 7:

(i) SEQUENCE CHARACTERISTICS:
        (A) LENGTH: 24 amino acids
        (B) TYPE: amino acid
        (D) TOPOLOGY: linear (xi) SEQUENCE DESCRIPTION: SEQ ID NO: 7:

```
Val  Ser  Ser  Leu  Leu  Ser  Ser  Leu  Leu  Ser  Ser  Leu  Lys  Glu  Tyr
                    5                        10                           15
Trp  Ser  Ser  Leu  Lys  Glu  Ser  Glu  Ser
                    20
```

( 2 ) INFORMATION FOR SEQ ID NO: 8:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO: 8:

```
Pro  Val  Leu  Asp  Glu  Phe  Arg  Glu  Lys  Leu  Asn  Glu  Glu  Leu  Glu
                    5                        10                       15
Ala  Leu  Lys  Gln  Lys  Met  Lys
                    20
```

( 2 ) INFORMATION FOR SEQ ID NO: 9:

( i ) SEQUENCE CHARACTERISTICS:
        ( A ) LENGTH: 22 amino acids
        ( B ) TYPE: amino acid
        ( D ) TOPOLOGY: linear ( x i ) SEQUENCE DESCRIPTION: SEQ ID NO: 9:

```
Pro  Leu  Ala  Glu  Asp  Leu  Gln  Thr  Lys  Leu  Asn  Glu  Asn  Val  Glu
                    5                        10                       15
Asp  Leu  Arg  Lys  Gln  Leu  Val
                    20
```

COMPOSITIONS USEFUL IN PROPHYLAXIS AND THERAPY OF ENDOTOXIN RELATED CONDITIONS

RELATED APPLICATIONS

This application is a continuation in part of Ser. No. 08/288,568, filed Aug. 10, 1994, now U.S. Pat. No. 5,506,218, which is a continuation-in-part of PCT Application PCT/US93/07453 filed Aug. 9, 1993 which is a continuation-in-part of U.S. patent application Ser. No. 07/928,930 filed Aug. 12, 1992, now U.S. Pat. No. 5,344,822. All of these applications and patents are incorporated by reference.

FIELD OF THE INVENTION

This invention relates to the treatment of endotoxin related endotoxemia. More particularly, it relates to the treatment of such poisoning via administration of various compositions which act to neutralize and/or remove endotoxins from the organism, as well as prophylaxis utilizing these compositions.

BACKGROUND AND PRIOR ART

Normal serum contains a number of lipoprotein particles which are characterized according to their density, namely, chylomicrons, VLDL, LDL and HDL. They are composed of free and esterified cholesterol, triglycerides, phospholipids, several other minor lipid components, and protein. Very low density lipoprotein (VLDL) transports energy, in the form of triglycerides, to the cells of the body for storage and use. As triglycerides are delivered, VLDL is converted to low density lipoprotein (LDL). Low density lipoprotein (LDL) transports cholesterol and other lipid soluble materials to the cells in the body, while high density lipoprotein (HDL) transports excess or unusable lipids to the liver for elimination. Normally, these lipoproteins are in balance, ensuring proper delivery and removal of lipid soluble materials. Abnormally low HDL can cause a number of diseased states as well as constitute a secondary complication in others.

Under normal conditions, a natural HDL is a solid particle with its surface covered by a phospholipid monolayer that encloses a hydrophobic core. Apolipoprotein A-I and A-II attach to the surface by interaction of the hydrophobic face of their alpha helical domains. In its nascent or newly secreted, form, the particle is disk-shaped and accepts free cholesterol into its bilayer. Cholesterol is esterified by the action of lecithin:cholesterol acyltransferase (LCAT) and is moved into the center of the disk. The movement of cholesterol ester to the center is the result of space and solubility limitations within the bilayer. The HDL particle "inflates" to a spheroidal particle as more and more cholesterol is esterified and moved to the center. Cholesterol ester and other water insoluble lipids which collect in the "inflated core" of the HDL are then cleared by the liver.

Anantharamaiah, in Segrest et al., Meth. Enzymol. 128:627–647 (1986) describes a series of peptides which form "helical wheels", as a result of the interaction of the amino acids in the peptide with each other. Such helical wheels present a nonpolar face, and a polar face in their configuration. The reference shows, generally, that peptides can replace aproproteins in these particles.

Jonas et al., Meth. Enzym. 128A: 553–582 (1986) have produced a wide variety of reconstituted particles resembling HDL. The technique involves the isolation and delipidation of HDL by standard methods (Hatch et al., Adv. Lip. Res. 6: 1–68 (1968); Scanu et al., Anal. Biochem. 44:576–588 (1971)) to obtain apo-HDL proteins. The apoproteins are fractionated and reconstituted with phospholipid and with or without cholesterol using detergent dialysis.

Matz et al., J. Biol. Chem. 257(8): 4535–4540 (1982) describe a micelle of phosphatidylcholine, with apolipoprotein A1. Various ratios of the two components are described, and it is suggested that the described method can be used to make other micelles. It is suggested as well to use the micelles as an enzyme substrate, or as a model for the HDL molecule. This paper does not, however, discuss application of the micelles to cholesterol removal, nor does it give any suggestions as to diagnostic or therapeutic use.

Williams et al., Biochem. & Biophys. Acta 875:183–194 (1986) teach phospholipid liposomes introduced to plasma which pick up apoproteins and cholesterol. Liposomes are disclosed, which pick up apoprotein in vivo, as well as cholesterol, and it is suggested that the uptake of cholesterol is enhanced in phospholipid liposomes which have interacted with, and picked up apoproteins.

Williams et al., Persp. Biol. & Med. 27(3): 417–431 1984) discuss lecithin liposomes as removing cholesterol. The paper summarizes earlier work showing that liposomes which contain apoproteins remove cholesterol from cells in vitro more effectively than liposomes which do not contain it. They do not discuss in vivo use of apoprotein containing liposomes or micelles, and counsel caution in any in vivo work with liposomes.

It is important to note that there is a clear and significant difference between the particles of the present invention, and the liposomes and micelles described in the prior art. The latter involve a bilayer structure of lipid-containing molecules, surrounding an internal aqueous core space. The structure of liposomes precludes filling the internal space with a lipid soluble component, however, and any molecular uptake of lipid soluble components is limited to the space defined between the two lipid layers. As a result, there is much less volume available for pick up and discharge of materials such as cholesterol and other lipid soluble materials than there is for the particles of this invention, which expand in a fashion similar to a balloon, with interior space filling with the material of choice.

Endotoxic shock is a condition, often fatal, provoked by the release of lipopolysaccharide (LPS) from the outer membrane of most gram negative bacteria (e.g., *Escherichia coli; Salmonella tymphimurium*). The structure of the bacterial LPS has been fairly well elucidated, and it comprises a unique molecule, referred to as lipid A, which is linked to acyl chains via lipid A molecule's glucosamine backbone. See Raetz, Ann. Rev. Biochem. 59:129–170 (1990) in this regard.

The lipid A molecule serves as membrane anchor of a lipopolysaccharide structure ("LPS") and it is the LPS which is implicated in the development of endotoxic shock. It should be pointed out that LPS molecules are characterized by a lipid A type structure and a polysaccharide portion. This latter moiety may vary in molecular details in different LPS molecules, but it will retain the general structural motifs characteristic of endotoxins. It would be incorrect to say that the LPS molecule is the same from bacteria to bacteria (see *Raetz, supra*). It is common in the art to refer to the various LPS molecules as "endotoxins" and this term will be used hereafter to refer to LPS molecules collectively.

In U.S. Pat. No. 5,128,318 the disclosure of which is incorporated by reference, it was taught that reconstituted particles containing both an HDL associated apolipoprotein and a lipid capable of binding an endotoxin to inactivate it could be used as effective materials for alleviating endotoxin caused toxicity.

In the parent and grandparent applications cited in the Related Application section and incorporated by reference herein, it was disclosed that various other materials may be used to treat endotoxin caused toxicity. Specifically, it was found that apolipoproteins are not required in reconstituted particles, and that the reconstituted particle may contain a peptide and a lipid wherein the peptide is not an apolipoprotein.

It was also found by the inventors that endotoxin caused toxicity may be treated via sequential administration of either an apolipoprotein or a peptide followed by a lipid. Following sequential administration, the components assemble as a reconstituted particle and then act to remove endotoxin.

It was also found that at least some individuals possess native levels of apoliprotein which are higher than normal levels such that effective endotoxemia therapy may be effectuated by administering reconstituted particles containing no apolipoprotein or peptide, but containing the lipid of the disclosure.

In addition, the invention disclosed in these applications involved the use of the reconstituted particles and the components discussed herein for prophylaxis against endotoxin caused toxicity, by administering prophylactically effective amounts to subjects in need of prophylaxis. Such subjects include patients suffering from infections or recovering from surgery. These patients sometimes have very low plasma HDL levels, sometimes as little as 20% of normal levels. It is highly desirable, in these cases, for early prophylaxis with HDL, so as to compensate for these drops.

It has now been found, quite surprisingly, that phospholipids may be used alone, or in combination with additional materials, such as neutral lipids, cholates, etc., as effective agents to alleviate and/or prevent endotoxemia. It is especially preferred to use phosphatidylcholines ("PC" hereafter), either alone, or in combination with other phospholipids, such as sphingolipids, in compositions which are essentially free of peptides and proteins, such as apolipoproteins or peptides derived therefrom. Neutral lipids such as mono-, di-, and triglycerides may be combined with the phospholipids, as long as the total amount of neutral lipids is below certain weight percents when the compositions are used in the form of an intravenous bolus. When used in other forms of administration, such as intravenously for example, by continuous infusion, the weight percents are not so critical, but are desirable.

Particularly preferred embodiments of the invention are those compositions where the neutral lipid is cholesterol ester, or a mixture of cholesterol ester and triglycerides.

The efficacy of bile acids and bile acid salts, which are cholates, in the treatment of endotoxemia is shown herein. These bile acids may be used alone, or in combination with one or more phospholipids, and/or neutral lipids, such as a phosphatidylcholine, and/or a triglyceride.

The invention is described in greater detail in the disclosure which follows.

BRIEF DESCRIPTION OF THE FIGURES

FIG. 5A shows the role of protein, and 5B that of phospholipid. The compositions tested included natural lipoproteins (VLDL, LDL, HDL), reconstituted HDL ("R-HDL"), and INTRALIPID® compositions, as well as emulsions containing phospholipid and protein.

DETAILED DESCRIPTION OF THE EMBODIMENTS

EXAMPLE 1

Studies were carried out to determine the survival rate of mice challenged with $S.\ tymphimurium$ endotoxin. Outbred male, Swiss-Webster mice received either saline (20 mice), reconstituted HDL particles (40 mice), or reconstituted peptide 18A (20 mice), via injection through the tail vein. The particulars of the injection materials are as follows:

a. HDL particles

Particles were prepared from apo-Hu-HDL (85%-AI; 15% AII and apo C), reconstituted with 95% pure egg phosphatidylcholine (2:1 W/W), using detergent dialysis, in accordance with Matz et al., J. Biol. Chem. 257:4535–4540 (1982), and U.S. Pat. No. 5,128,318, the disclosure of which is incorporated by reference.

b. peptide particles

The peptide 18A has the amino acids sequence: Asp-Trp-Leu-Lys-Ala-Phe-Tyr-Asp-Lys-Val-Ala-Gly-Lys-Leu-Lys-Glu-Ala-Phe SEQ ID NO:1

Samples of peptide were also mixed and reconstituted with 95% pure eggs phosphatidylcholine as per Matz et al., supra (2:1 w/w), and U.S. Pat. No. 5,128,318 also using detergent dialysis. The resulting particles are identical to those disclosed in U.S. Pat. No. 5,128,318 except that a peptide component was present, rather than the apo-HDL of the Matz and patent references.

Figure 3:
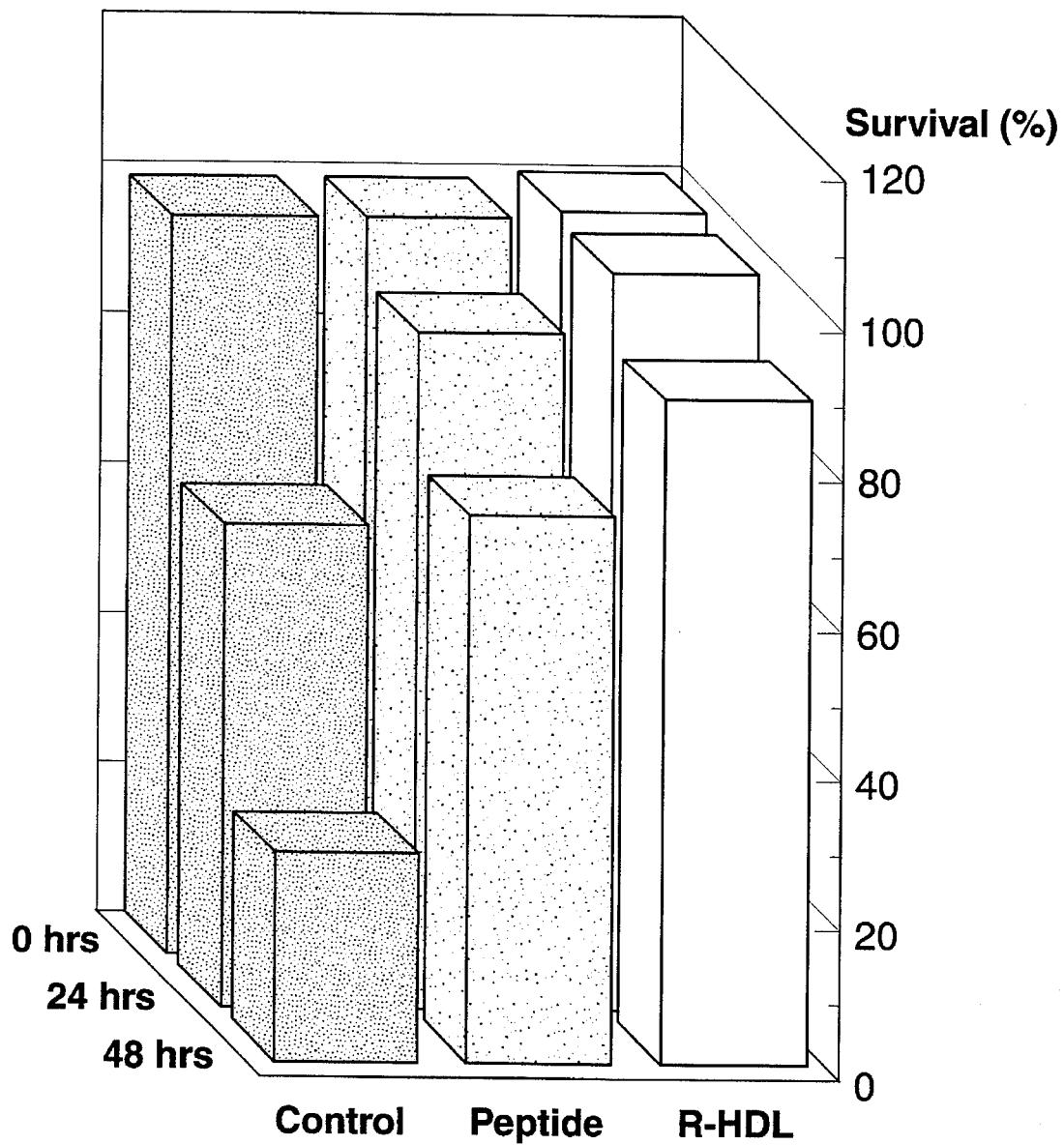
FIG. 3 shows experiments in which a peptide in accordance with the invention as used to study reduction of endotoxin caused toxicity in a mouse model.
Figure 4A:
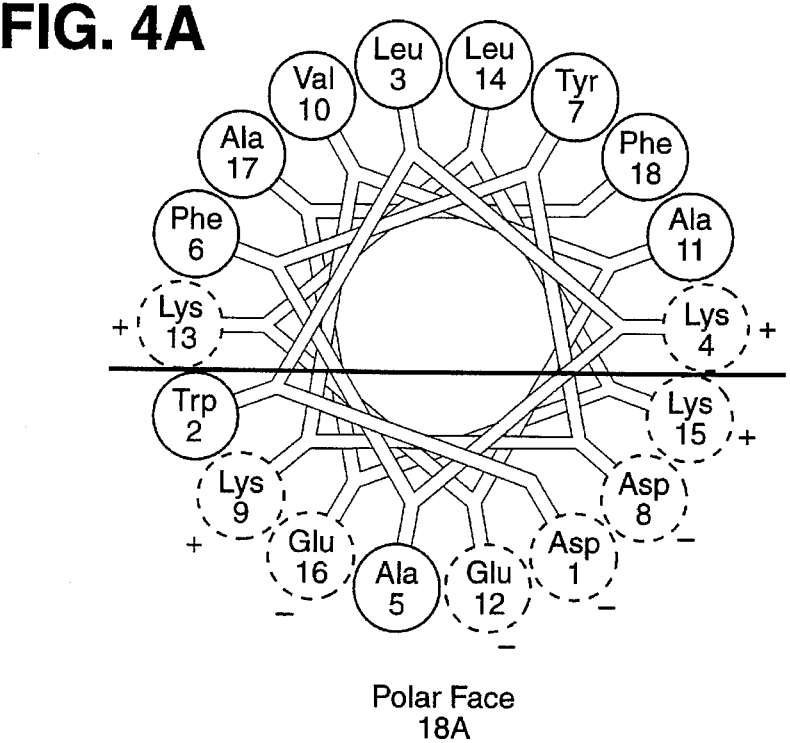
FIG. 4, labelled prior art, shows the formation of helical wheels by various peptides. See Anantharamaiah, supra.
Figure 4B:
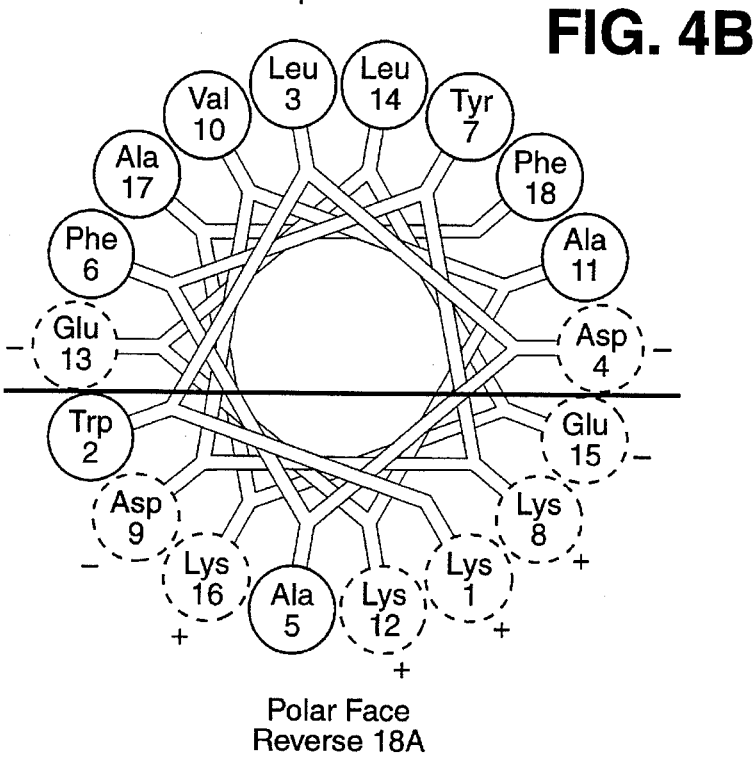
Figure 4C:
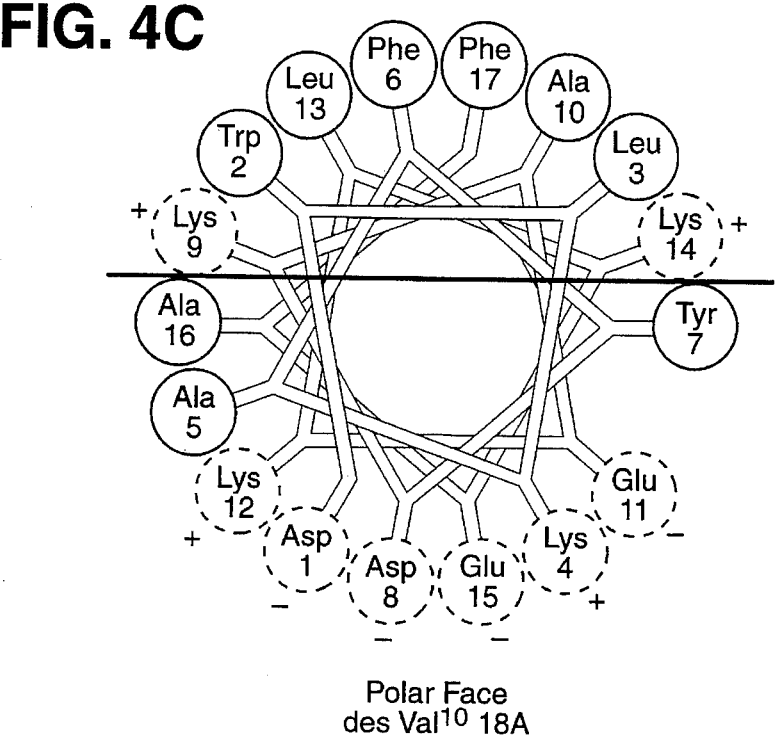
Figure 4D:
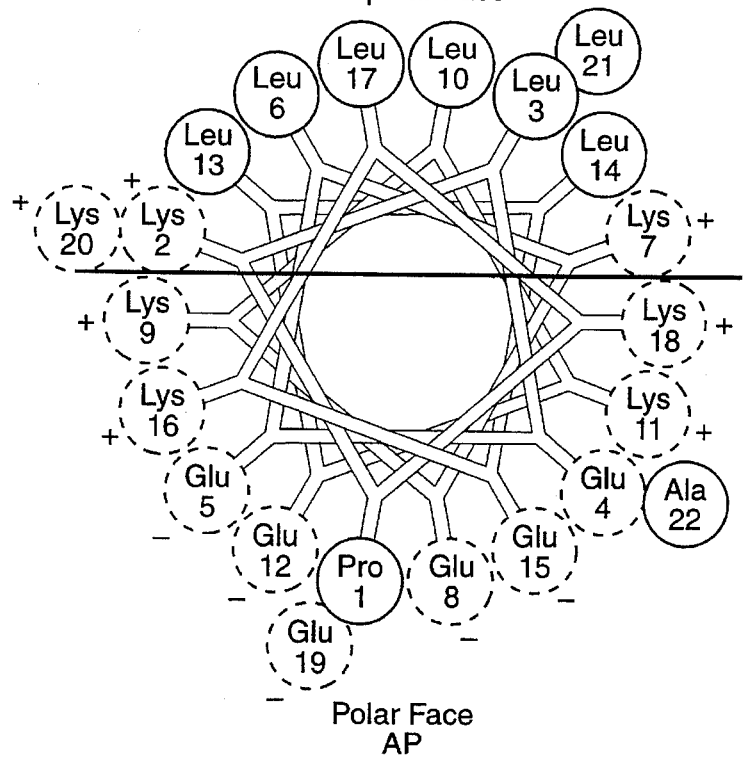
Figure 4E:
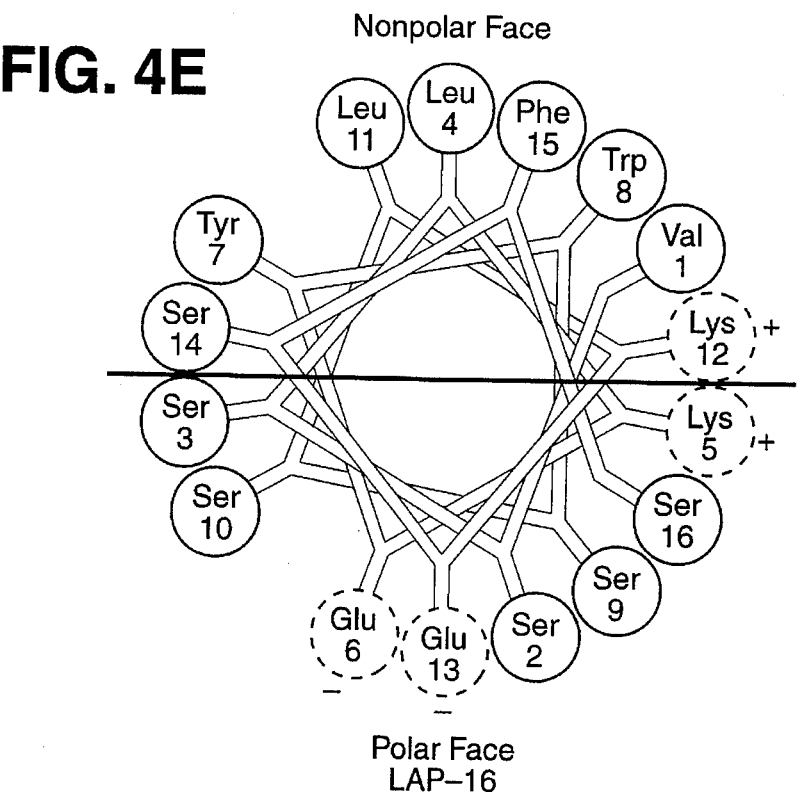
Figure 4F:
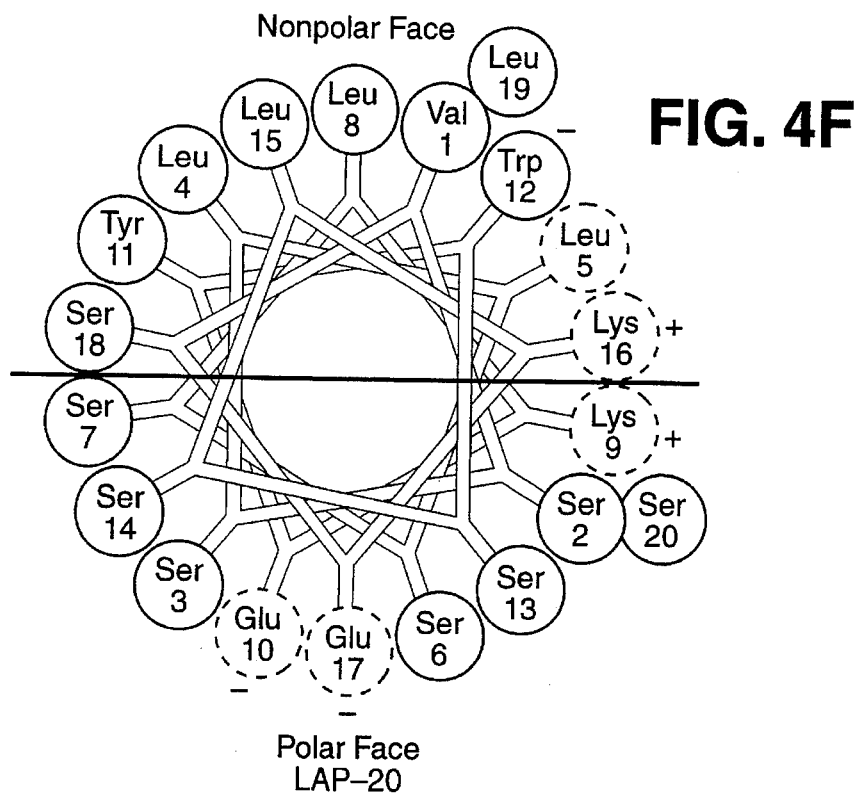
Figure 4G:
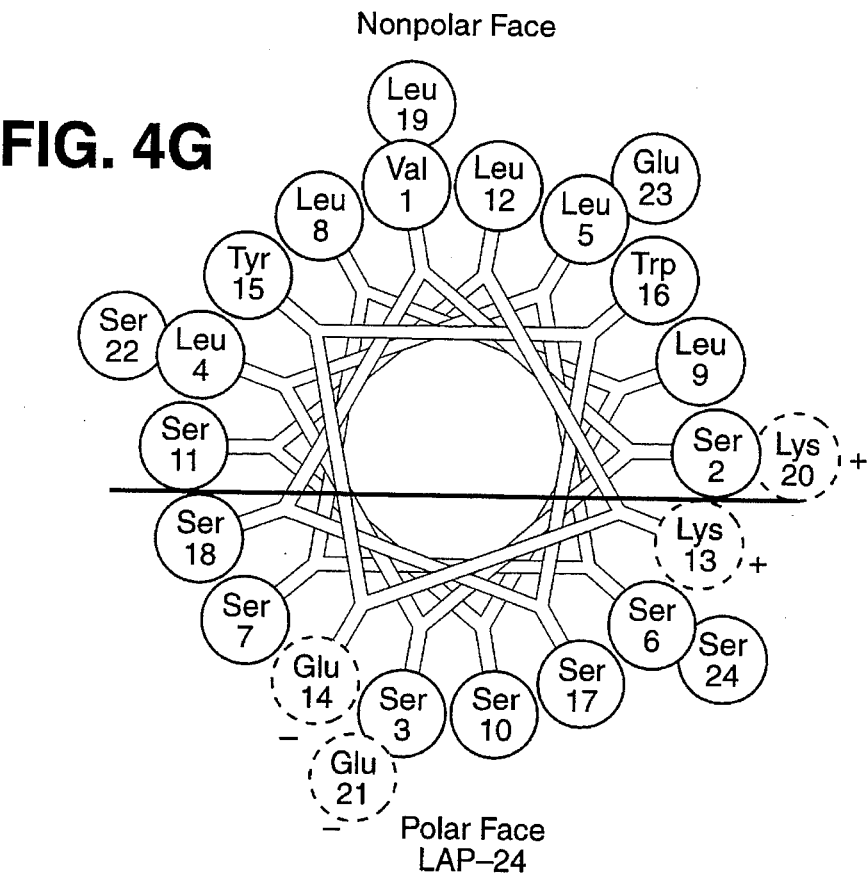
Figure 4H:
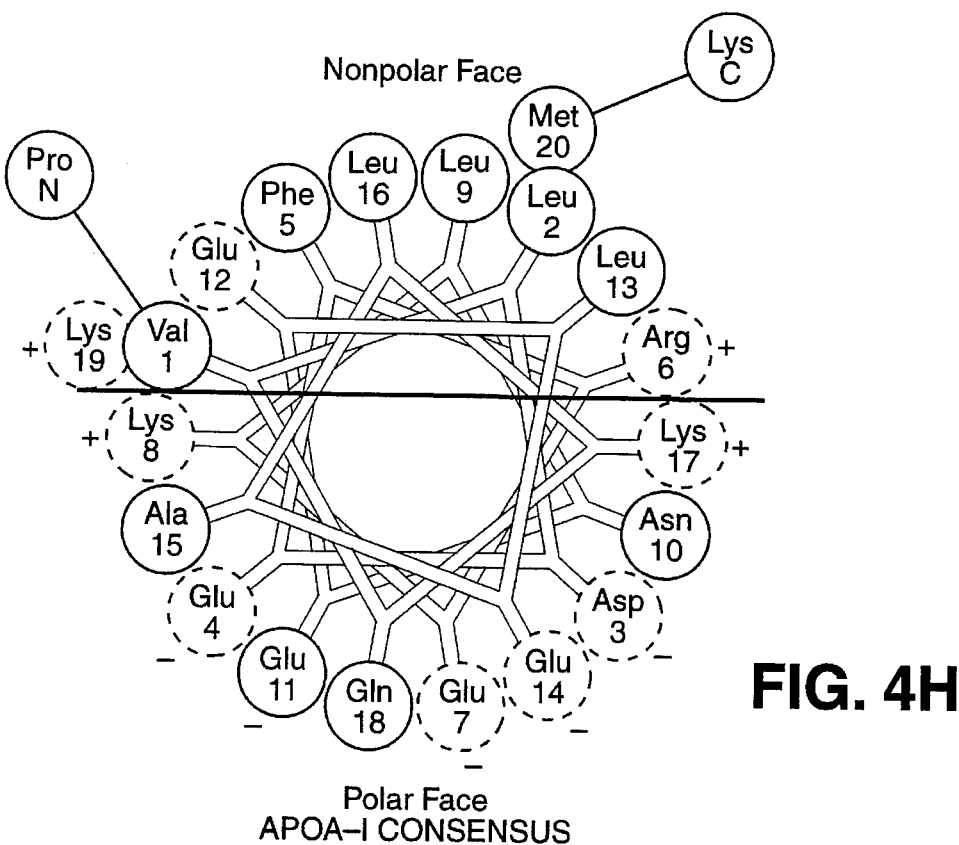
Figure 4I:
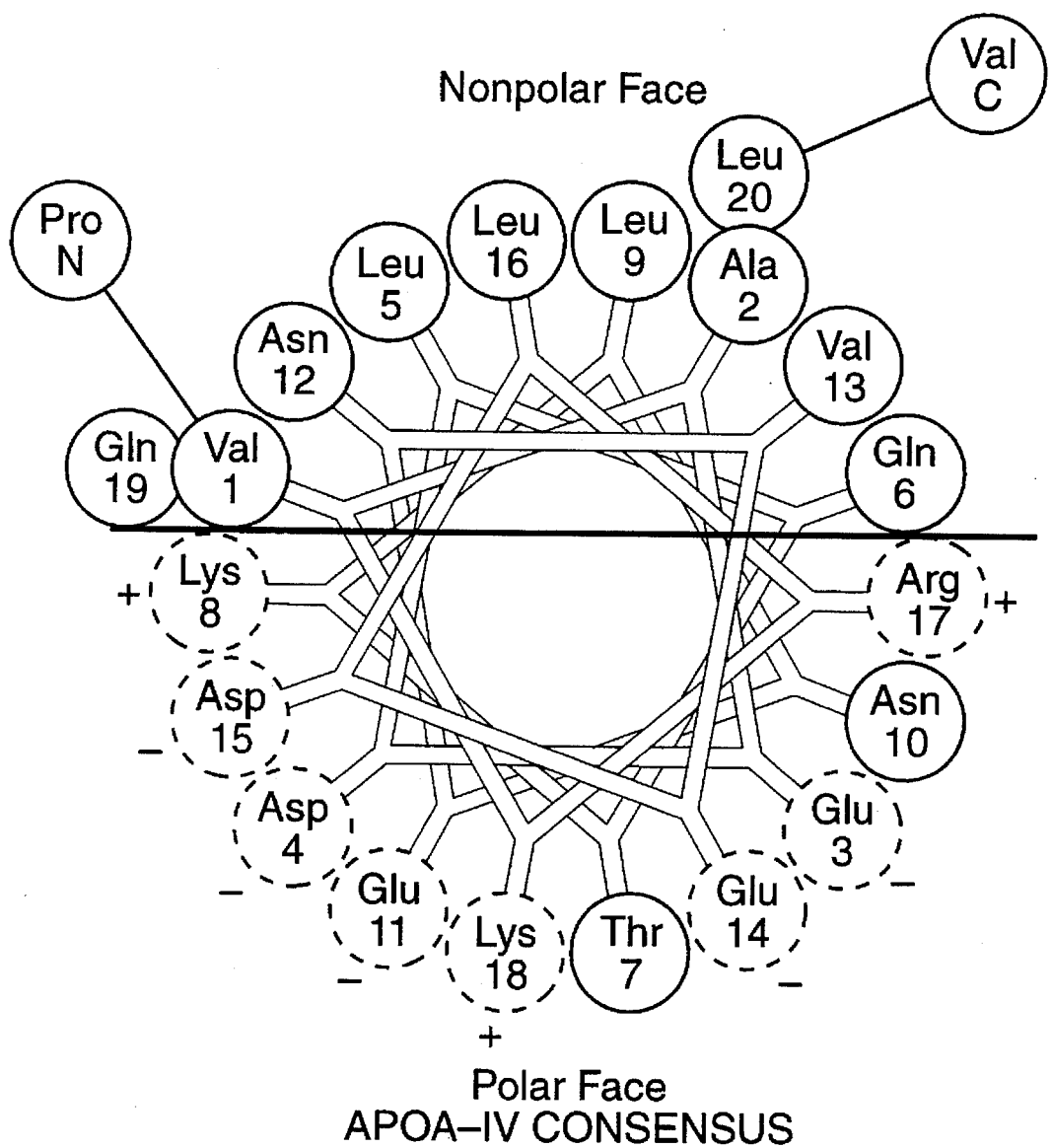

Within fifteen minutes of administration of the reconstituted material, the mice were administered, intraperitoneally, 10 mg/kg body weight of Salmonella LPS. The criterion for evaluation was survival. FIG. 3 presents these results, and indicates nearly 4 fold superiority over the saline control. The synthetic peptide is almost as effective as the reconstituted apo-HDL containing particles.

EXAMPLE 2

Factors which affect the LPS-mediated stimulation of TNF-α while preserving the integrity of interaction between plasma proteins, and cellular elements of blood, can be appropriately studied in an in vitro, human whole blood system. Such a system was used to determine which of the components of lipoproteins is important in neutralizing LPS.

Materials tested were reconstituted high density lipoprotein (R-HDL), natural plasma lipoproteins (VLDL, LDS, HDL), lipoprotein deficient serum (LPDS), and the triglyceride rich emulsion 20% INTRALIPID® (a mixture of triglycerides and phospholipids).

All particles described herein were made via the same protocol, which involved mixing a phospholipid, sphingomyelin or phosphatidylcholine, triolein, and/or unesterified cholesterol ester, dissolved in chloroform, and weighing it into a flask. Vitamin E (0.02% w/v) was added as antioxidant. A dry lipid film was then prepared by blowing nitrogen or argon gas over the sample. A volume of non pyrogenic saline was then added to the flask, followed by mixing on a vortex mixer until all lipid was suspended. The solution was then homogenized in a high pressure homogenizer. Samples containing phosphatidylcholine (PC), with or without triolein, were cycled through the homogenizer 10 times at 20,000 psi. Samples containing cholesterol ester with one or more other lipids were cycled through 15–20 times at 30,000 psi. Homogenized solutions were filtered through 0.45 μm syringe filters, and the filtrate was stored at room temperature until used (within three days).

Blood was collected in a heparinized tube, diluted with Hank's Balanced Salt Solution ("HBSS" hereafter), or the material to be tested, dissolved in HBSS. The resulting material was transferred to Starstedt tubes (250 ul/tube). LPS was dissolved in pyrogen free saline containing 10 mM HEPES, and added (2.5 ul) to a final concentration of 10 ng/ml. After incubation for four hours at 37° C., tubes were chilled to 4° C. followed by centrifugation at 10,000xg for 5 minutes. Supernatant was collected, and assayed for determination of TNF-α, using a commercially available ELISA.

Figure 5A:
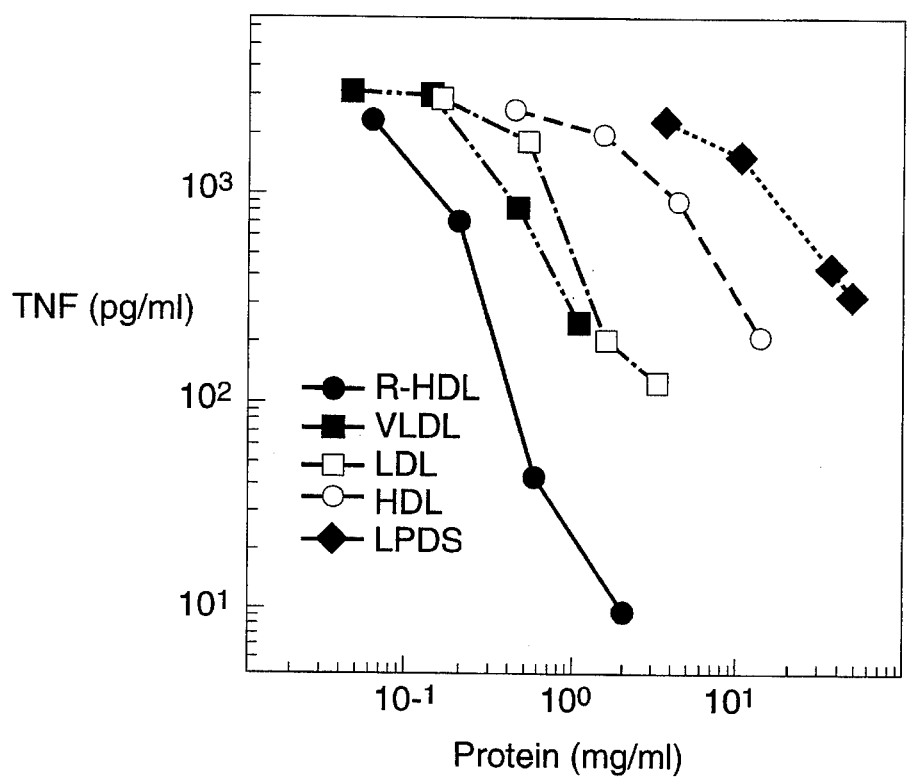
FIGS. 5A and 5B show results obtained when various compositions were tested in a model which determined the neutralization of endotoxin via determining TNF release in a human whole blood model.
Figure 5B:
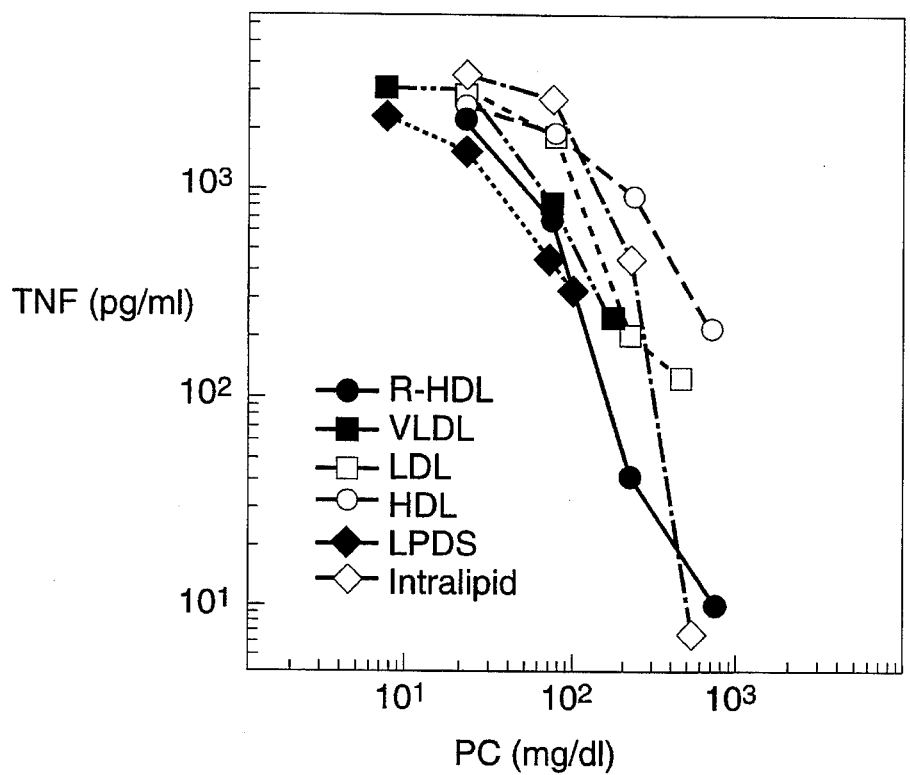

Table 1, which follows, compares the compositions of the materials tested. FIGS. 5A and 5B present the results. Data are plotted as amount of TNF-α produced, plotted against concentration of added protein (FIG. 5A), and phospholipid (FIG. 5B). Logarithmic scales were used, in order to display the wide range of concentrations used, with $10^0$ equal to 1 mg/ml. All whole blood incubations contained 10 ng/ml of E. coli 0111:B4 LPS, supplemented with one of the compositions, as the key for FIGS. 5A and 5B shows.

The fact that the materials differ in effectiveness when protein content is plotted (FIG. 5A), while being very similar when phospholipid content is plotted (FIG. 5B) suggest that the phospholipid is the important component. This is confirmed by the finding that a protein free lipid emulsion is more effective than is natural HDL, but less effective than R-HDL. Protein does not appear important to the neutralization.

Composition of natural lipoproteins and reconstituted HDL

| Lipoprotein | | TC | TG | PC | Protein |
|---|---|---|---|---|---|
| Class | Density (g//ml) | | Weight % | | |
| VLDL | <1.006 | 22 | 53 | 18 | 7 |
| LDL | 1.007–1.063 | 48 | 11 | 22 | 20.9 |
| HDL | 1.063–1.21 | 18 | 8 | 22 | 52 |
| R-HDL | 1.063–1.21 | — | — | 79 | 21 |
| LPDS | >1.21 | 0 | 0 | 2 | 98 |
| Intralipid | — | 1 | 93 | 6 | 0 |

EXAMPLE 3

Figure 6A:
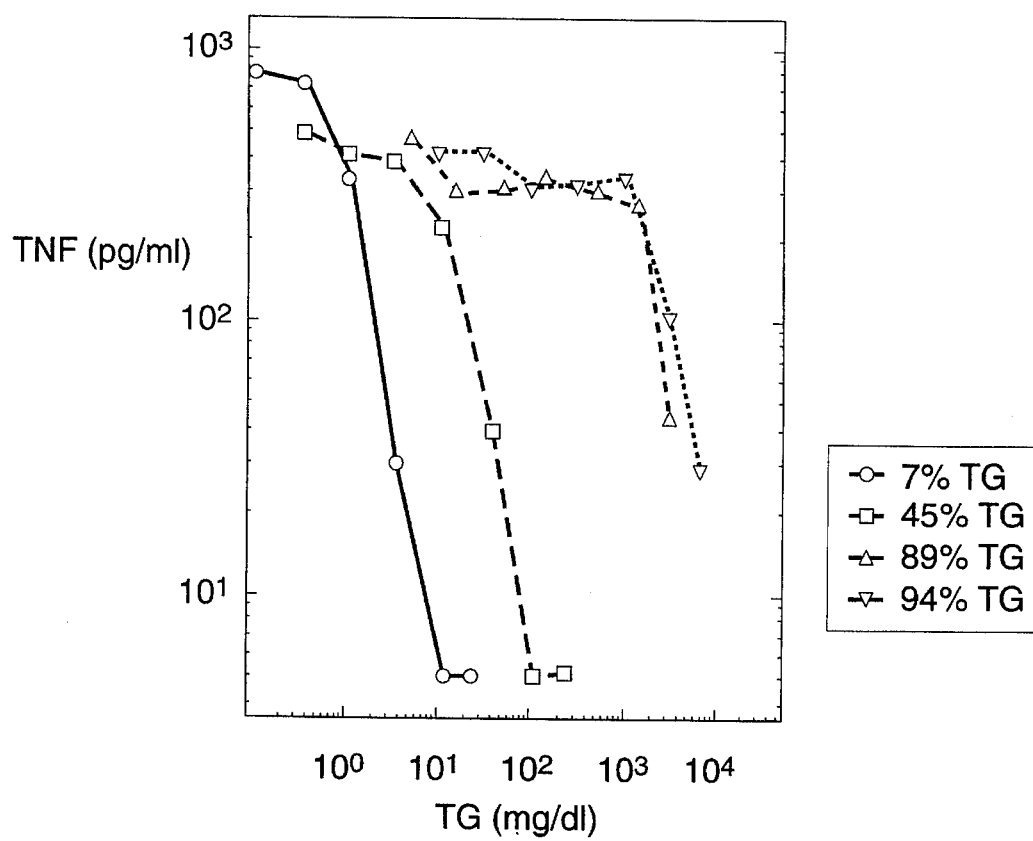
FIGS. 6A and 6B compare the role of triglyceride (a neutral lipid), and phosphatidylcholine, a phospholipid, in the same model.
Figure 6B:
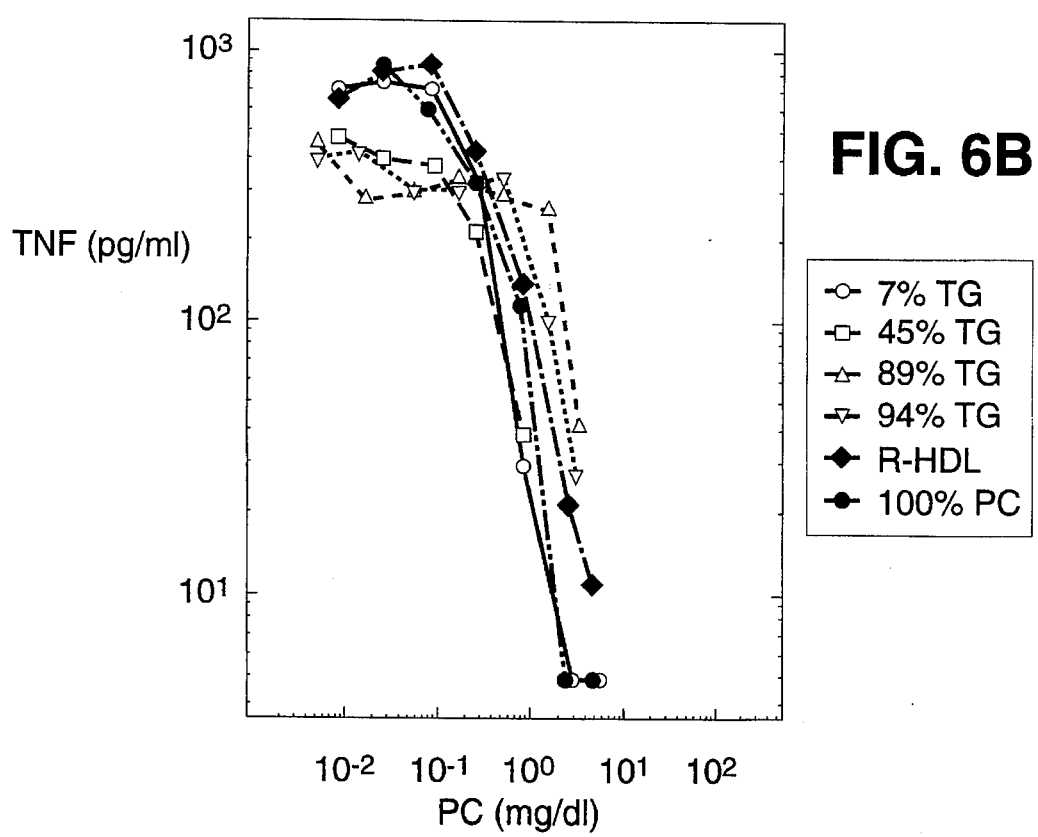

As the next step, protein free lipid emulsions, containing different amounts of neutral lipid, were tested in human whole blood. The same in vitro human whole blood assay as set forth in example 2 was used. FIGS. 6A and 6B present these results. In these studies, LPS-dependent, TNF-α production is plotted against concentration of added triglyceride (FIG. 6A), or phospholipid (FIG. 6B). The compositions, as indicated by the key, contained (by weight) 7% triglyceride ("TG"), 45% TG, 89% TG, 94% TG, R-HDL, or phospholipid without TG, (shown in FIG. 6B only). An 89% TG composition is a 10% INTRALIPID® formulation, while 94% TG refers to 20% INTRALIPID. In all other tests, egg phosphatidylcholine (PC), and triolein were used.

These results show that the protein free compositions, when compared via triglyceride content, are very different. They are very similar when tested via phospholipid (PC) content. This confirms the role of phospholipid, especially since phospholipid alone is effective, but less so than emulsions containing up to 45% TG.

EXAMPLE 4

The work then proceeded to in vivo experiments in a mouse model, which is accepted as a reliable system for predicting human efficacy.

Figure 7:
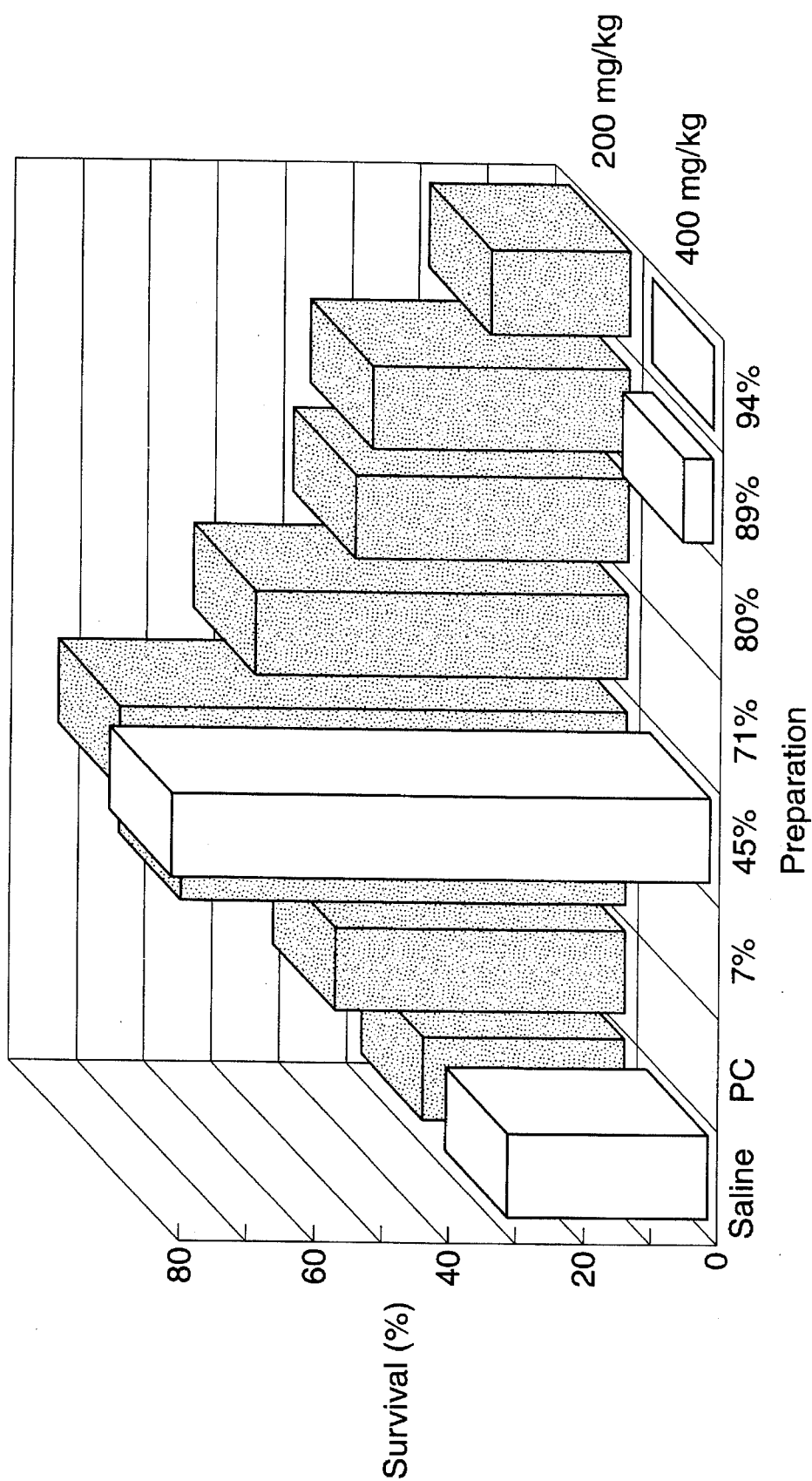
FIG. 7 presents reported information on toxicity associated with administration of various PC and PC/TG compositions in a mouse model, using a 70% toxicity model where $E.\ coli$ LPS is administered.

In these experiments, mice were injected, in bolus form, with sufficient amounts of the formulations described in example 3 as well as others (pure phosphatidylcholine, 7% TG, 45% TG, 71% TG, 80% TG, 89% TG, 94% TG), or a saline control, to provide doses of phospholipid (either 200 mg/kg or 400 mg/kg), together with 25 mg/kg of E. coli 0111:B4 LPS. The control group received intravenous physiological saline in a volume sufficient to match the volume of emulsion. Survival after 72 hours is presented in FIG. 7.

Overall survival in the control group was 29%±8% (mean: 63 animals in 8 experiments). Each preparation was tested in a minimum of 3 experiments on 18 or more animals.

PC alone had a modest protective effect, not statistically significant at the 95% confidence level, while 7%, 45% and 71% TG compositions significantly improved survival. The 80% and 89% TG compositions were marginally effective, while the 94% TG decreased survival.

When the dose was increased to provide 400 mg/kg of PC both the 89% and 94% TG emulsions significantly decreased survival time, probably due to TG poisoning, as explained infra.

EXAMPLE 5

The work described in examples 2–4 established that phospholipids are an active agent useful in inhibiting endotoxemia. The fact that non-polar lipids other than triglycerides may form emulsions with phospholipids other than PC suggested that others may be tried. Exemplary are spingomyelin (another phospholipid), and unesterified cholesterol (a polar neutral lipid), and mixtures of these. So, too, esterified cholesterol (a nonpolar ester), squalene (a hydrocarbon), and vitamin E (a nonpolar antioxidant) may be used. A series of experiments were designed to test these, using the human whole blood assay of example 2, supra, and the mouse survival assay of example 4.

Emulsions were prepared, in the manner described supra, using pure phosphatidylcholine, phosphatidylcholine with 10% (wt/wt) unesterified cholesterol, 10% (wt/wt) sphingomyelin, or 10% total of a mix of both. Emulsions were added to whole blood, at a concentration of 100 mg/dl, with reference to PC, and 10 ng/ml of LPS. The mixture was incubated, and TNF-α release measured.

Figure 8:
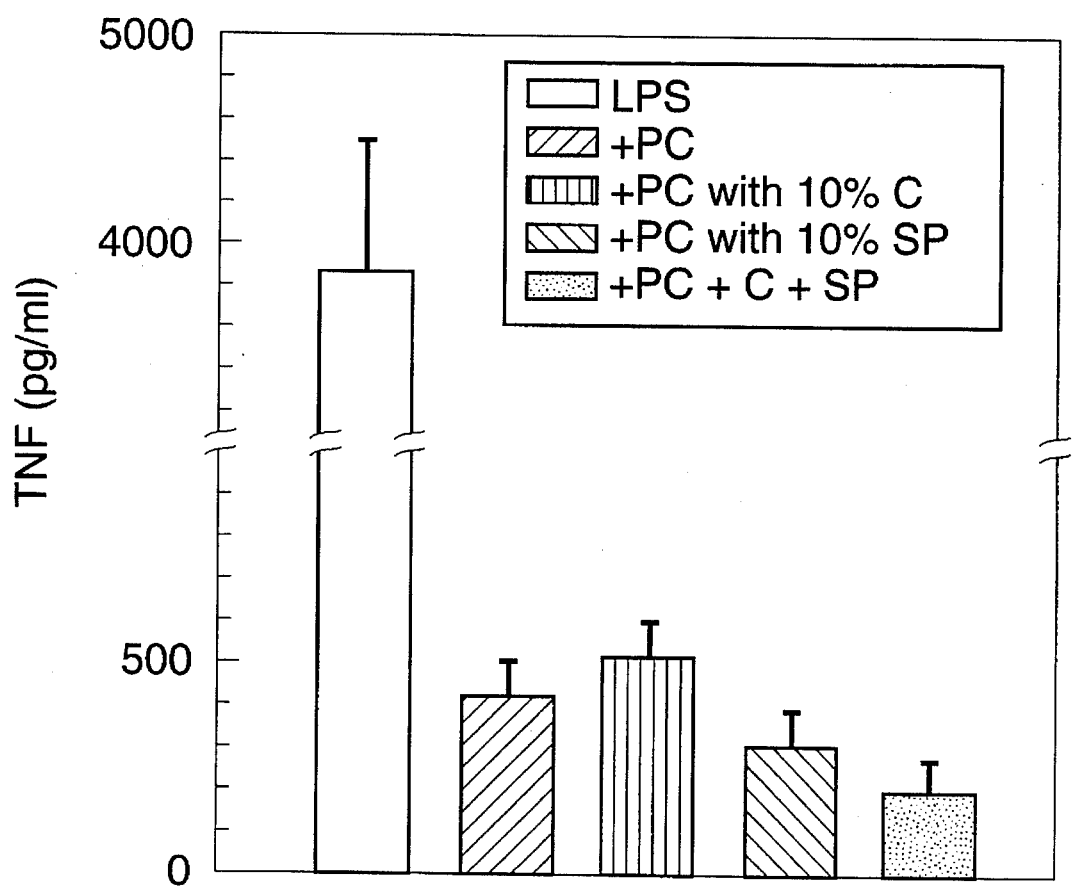
FIG. 8 shows data comparable to that secured for the human whole blood assay, supra, but using phospholipid with unesterified cholesterol, sphingomyelin, or mixtures of both, in place of triglycerides.

The results are shown in FIG. 8. TNF-α production was substantially reduced with PC alone. Emulsions containing unesterified cholesterol, sphingomyelin, or the mix of both, were also suppressive of TNF-α release.

EXAMPLE 6

The whole blood assay was also used to determine the effect of unesterified cholesterol and/or sphingomyelin to neutral lipid containing emulsions. Again, the emulsions were added at 100 mg/dl PC. The various compositions (wt/wt) are set forth in the following table.

| Emulsion | Composition |
| --- | --- |
| PC with 45% TG | 55:45 |
| PC + TG + C | 54.4:45.3:0.3 |
| PC + TG + SP | 51.6:43.0:5.4 |
| PC + TG + C + SP | 51.4:42.9:0.3:5.4 |
| PC + CE | 54.5:45.5 |
| PC + CE + C | 54.4:45.3:0.3 |
| PC + CE + SP | 51.6:43.0:5.4 |
| PC + CE + C + SP | 51.5:42.9:0.3:5.4 |

Figure 9A:
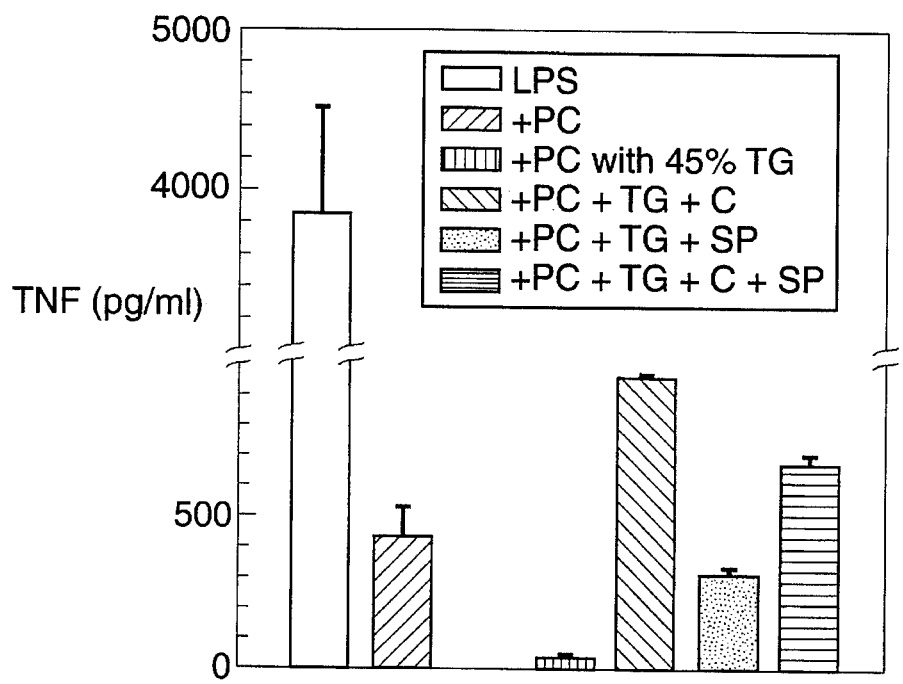
FIGS. 9A and 9B show results comparable to those shown in FIGS. 5A and 5B, except that in these new figures, phospholipid, unesterified cholesterol and/or sphingomyelin are mixed with triglycerides or esterified cholesterol as the neutral lipid.
Figure 9B:
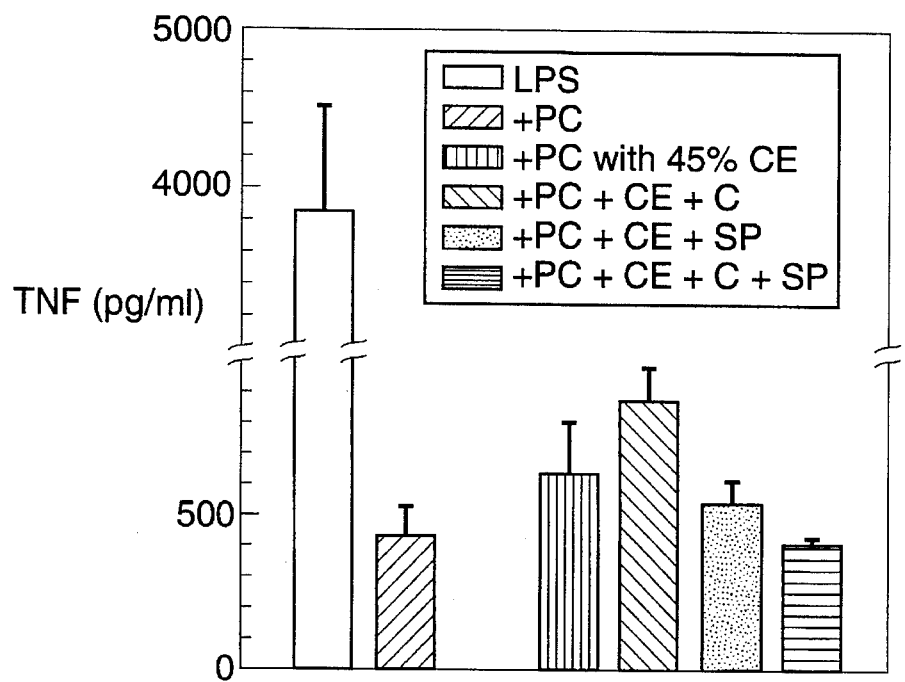

FIGS. 9A and 9B display the results. PC emulsions made with either neutral lipid, with or without additional polar lipids, demonstrated inhibition. Again, the LPS concentration used is a 70% lethal dose. The cholesterol ester containing emulsions are less effective than are TG containing emulsions, while those emulsions containing unesterified cholesterol did not suppress TNF-α as well as those emulsions which did not contain it. Adding sphingomyelin to the emulsions appeared to improve suppression of TNF-α production.

EXAMPLE 7

Cholesterol ester containing emulsions were tested in an in vivo model (i.e., that used in example 4), with a lethal dose of endotoxin. Emulsions were prepared with PC and TG, or PC and cholesterol ester (CE), and were administered to provide a single bolus dose of 200 mg/kg of PC, together with 25 mg/kg of E. coli 0111:B4 LPS (a lethal dose), through the tail vein. Control groups received intravenous physiological saline in a volume to match the volume of emulsion.

Figure 10:
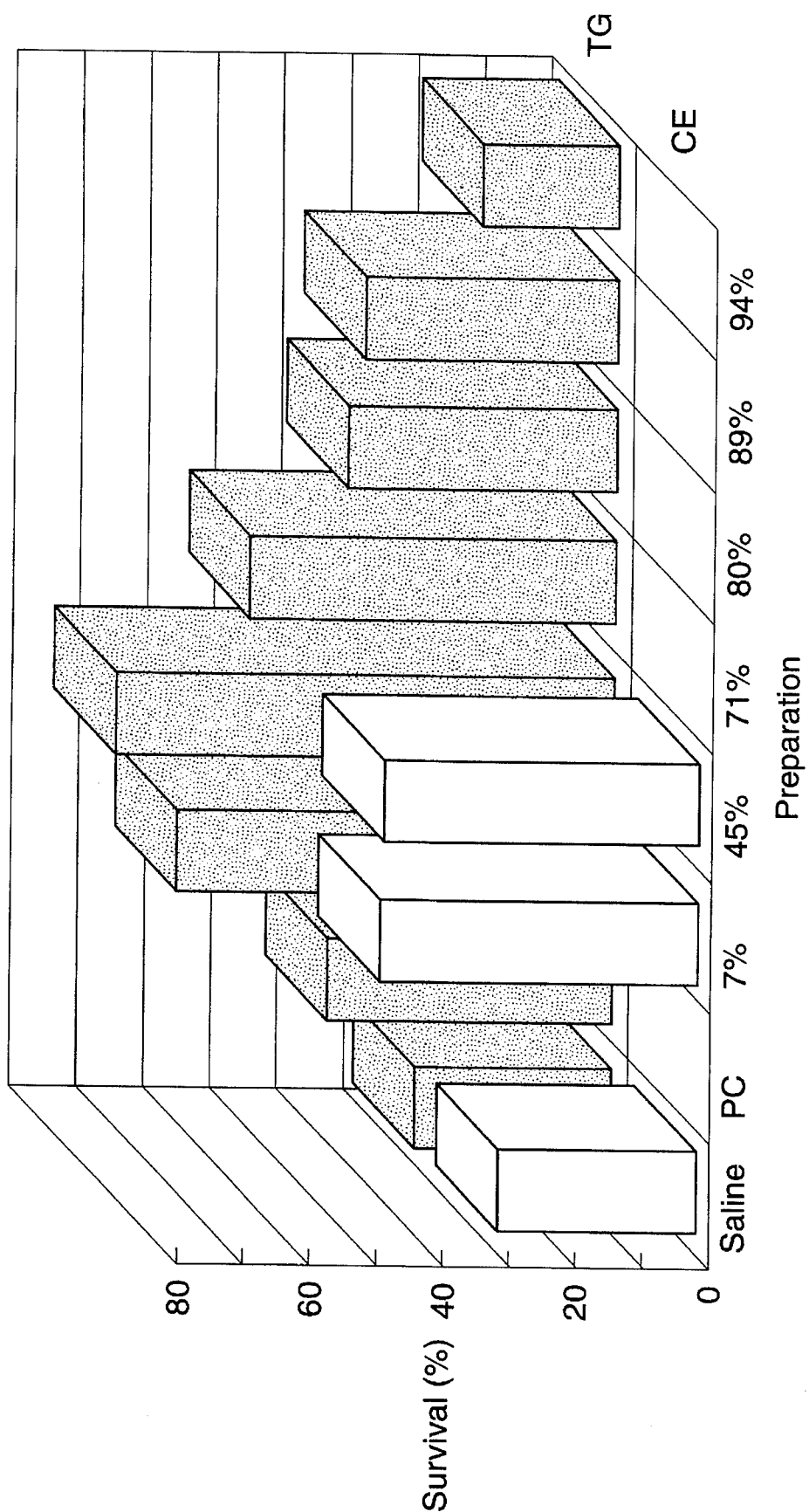
FIG. 10 compares results obtained from cholesterol ester and triglyceride containing emulsions, in the in vivo mouse model.

In FIG. 10, the data compare the results from the CE and TG containing emulsions. Each emulsion was tested in a minimum of two experiments, using a total of 16 or more animals.

As shown, emulsions containing 7% or 45% CE (wt %) significantly improved survival. These results, taken with those of example 6, show that CE can be substituted for TG to create emulsions that neutralize endotoxin.

EXAMPLE 8

Figure 11:
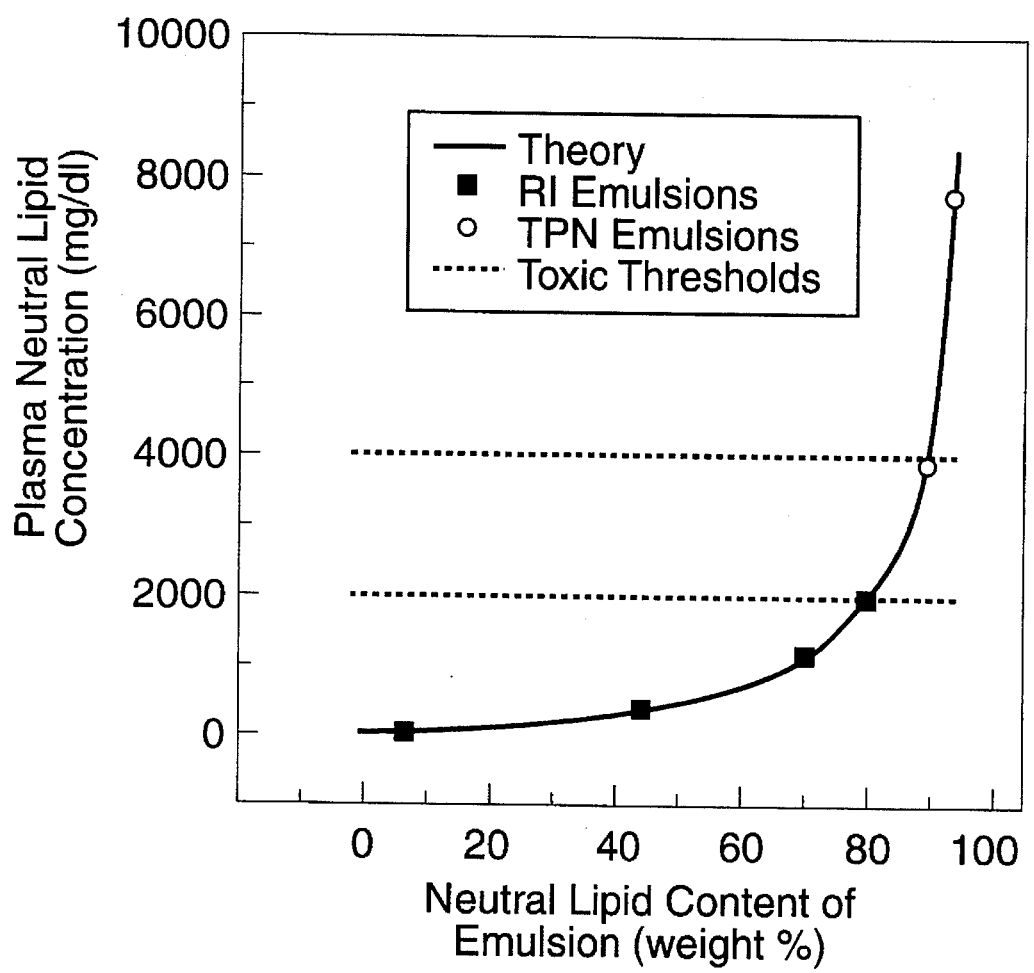
FIG. 11 graphs the theoretical amounts of triglycerides released into the blood following administration of various TG containing compositions, with toxicity thresholds. "TPN" stands for "total parenteral nutrition" while "RI" stands for compositions in accordance with the invention.

Protein-free emulsions of phospholipid with triglyceride effectively block TNF-α production in whole blood stimulated with LPS. In theory, these emulsions might also be effective in vivo if they can be administered safely in doses that provide protective concentrations of phospholipid in plasma. Our previous experiments with R-HDL suggest that the minimum dose of phospholipid is approximately 200 mg/kg. Using this dose and a plasma volume of 4.5% of body weight, one can calculate the concentration of triglyceride expected in plasma following administration of a series of emulsions with increasing triglyceride content. The result is shown in FIG. 11 as a smooth line curving upward with increasing weight percent TG. Plasma TG concentrations rarely rise above 1000 mg/dl in healthy adults even after a fatty meal. Pancreatitis is reported in patients with plasma TG above 2000 mg/dl (Farmer, et al., Amer. J. Med. 54:161–164 (1973); Krauss, et al., Amer. J. Med. 62: 144–149 (1977); Glueck, et al., J. Lab. Clin. Med. 123: 59–61). Plasma TG above 4000 mg/dl is extremely rare and cause for serious concern. The last two thresholds are shown by horizontal lines in the figure above. Administration of either 10% or 20% INTRALIPID® in a dose to provide 200 mg/kg phospholipid is expected to raise plasma TG concentrations (see the two open circles) well above the safe limits. By contrast, administration of emulsions containing 7%, 45%, 71% or 78% (solid squares left to right) raises plasma TG to 136, 477, 1300 or 2000 mg/dl respectively. Emulsions with TG content up to ~50% are expected to be free of toxicity from TG.

EXAMPLE 9

The efficacy of combinations of phospholipid and a bile acid, i.e., sodium cholate, was tested in the same type of experiment set forth in the previous examples.

Endotoxin purified from E. coli 0111B4 (40 mg/kg), and emulsion, as discussed infra (200 mg phosphatidylcholine/kg), were mixed at room temperature, and immediately administered to C57BL6/J mice (weight between 19 and 30 g), via intravenous injection through the tail vein. Those mice which received cholate alone were given a volume of sodium cholate equal to the cholate/EML (emulsion) preparation, at the same cholate concentration. The control mice received the same volume of 5% dextrose, so as to match plasma osmolality.

The results are set forth in the Table which follows immediately. The emulsion is the phosphatidyl/choline/7% triglyceride emulsion described in the preceding examples. Sodium cholate, when used, was added at the indicated concentration, to the raw materials, prior to the emulsification of the materials.

TABLE 1

Protection of Mice from Lethal Endotoxin Challenge.

| Time hrs | Control | 7% TG | 7% TG + CA | | | 18 mM CA | |
|---|---|---|---|---|---|---|---|
| | | | 9 mM | 18 mM | 36 mM | no PC or TG | +PC |
| | | | Survivors (N) | | | | |
| 0 | 28 | 28 | 8 | 16 | 8 | 8 | 8 |
| 24 | 9 | 12 | 4 | 15 | 8 | 8 | 8 |
| 48 | 5 | 10 | 2 | 15 | 8 | 8 | 8 |
| 72 | 2 | 5 | 1 | 15 | 8 | 8 | 8 |
| 96 | 1 | 0 | 1 | 15 | 8 | 7 | 8 |

For convenience, weight percentages of the emulsions are as follows. When 9 mM cholate was used, the percentages by weight relative to the emulsion are 7% cholate, 6.1% triglyceride, and 86.9% phosphatidylcholine. At 18 mM cholate, the weight percentages are 13.1% cholate, 5.7% triglyceride, and 81.2% phosphatidylcholine. At 36 mM cholate, the relative values are 23.2% cholate, 5% triglyceride, and 71.8% phosphatidylcholine.

It should be noted that the amount of LPS administered in these experiments (40 mg/kg), is much higher than the amount used for lethality studies in the prior experiments. The intent of these higher doses is to overwhelm any protective effect attributable to phosphatidylcholine and/or triglyceride. Thus, the conclusion to be reached following these experiments is that there is a protective effect attributable to the bile acid, salt sodium cholate.

Not presented herein are studies carried out using the bile acid salts sodium deoxycholate, and sodium chenodeoxycholate. Additional examples of useful materials include allodeoxycholic acid, lithocholic acid, hyodeoxycholic acid, hyocholic acid, α, β and ω-muricholic acids, murodeoxycholic acid, ursodeoxycholic acid, ursocholic acid, and all of the salts of these, such as their sodium salts. See Hoffmann, supra.

The foregoing examples detail the invention which involves, in one aspect, the alleviation or prevention of endotoxemia in a subject via administering an effective amount of a phospholipid with which an endotoxin associates. The association of phospholipid and endotoxin is then removed from the subject via standard biological processes well known to anyone familiar with processes via which lipoprotein particles are removed. Association of the endotoxin with the phospholipid inactivates it.

Figure 1:
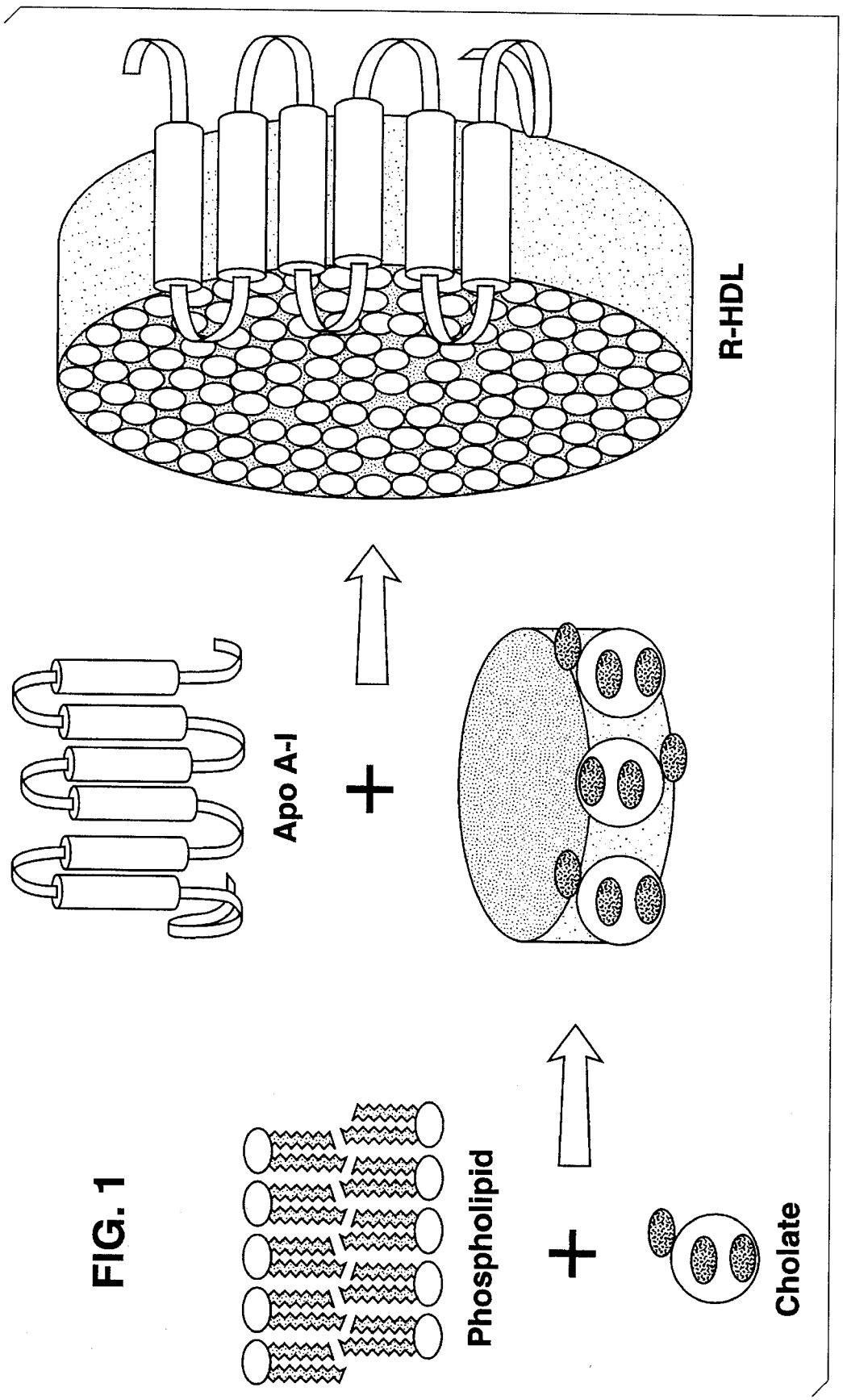
FIG. 1 shows how reconstituted particles containing Apo-A1, phospholipid and cholate form.
Figure 2:
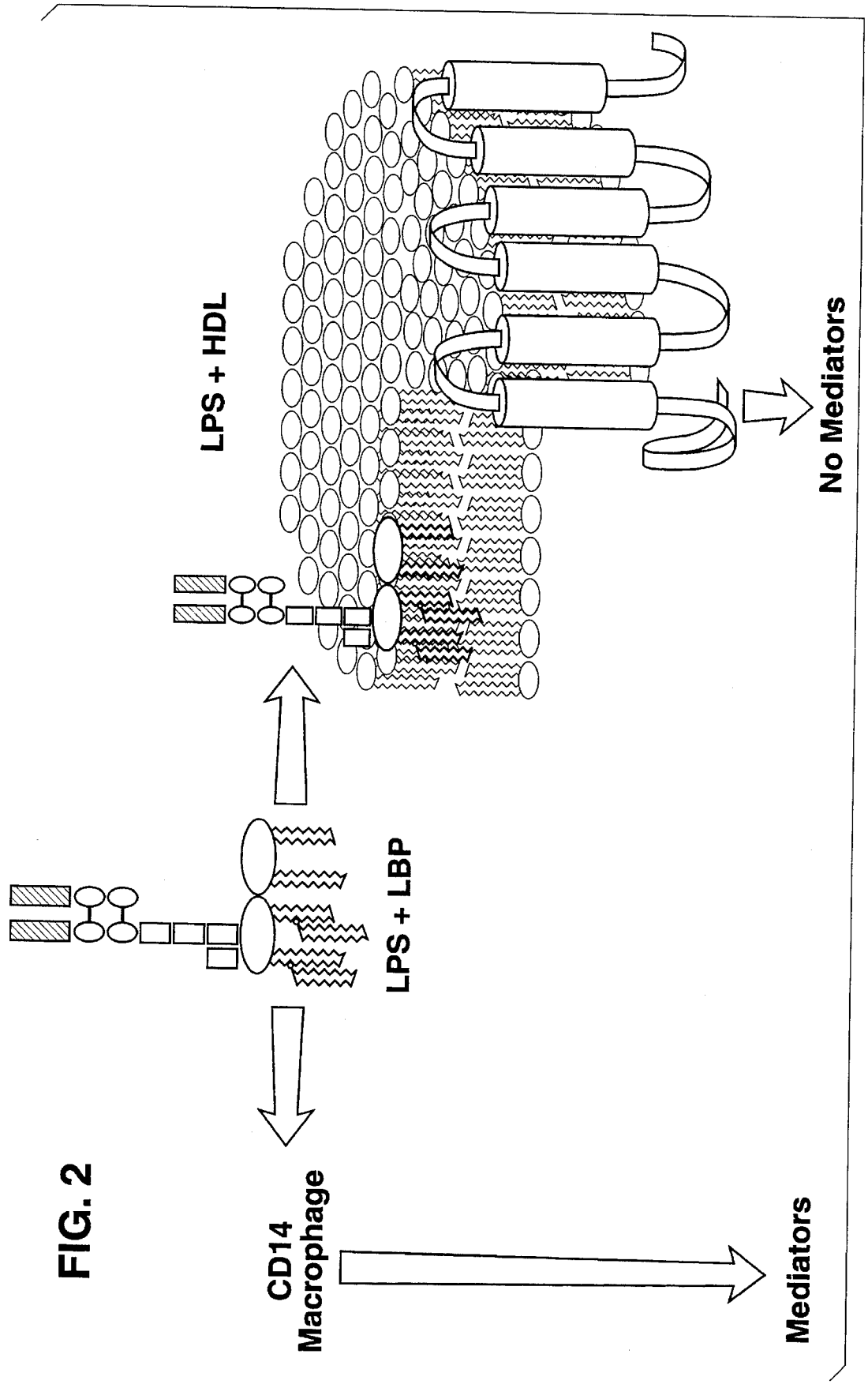
FIG. 2 shows the reception of LPS molecules by reconstituted particles.

The examples also show that administration of a member of the family of cholanoic acids or cholanoic acid salts, such as a bile acid or a bile acid salt can also be used to achieve the same end as the phospholipids, i.e., the alleviation or prevention of endotoxemia. Thus, peptide and protein free compositions containing one, or both of a bile acid/bile acid salt and a phospholipid may be used to treat endotoxemia. Cholanoic acids are described by, e.g., Hofmann, Hepatology 4(5): 4S-14S (1984), incorporated by reference. Attention is drawn in particular to page 5S, FIGS. 1 and 2, incorporated by reference, showing the structures characteristic of the cholanoic acids.

The subject being treated is preferably a human, but the practice of the invention is equally applicable in a veterinary context as well.

"Alleviation" as used herein refers to treatment to ease the burden of endotoxemia caused by any of the various endotoxins produced by, e.g., gram negative bacteria (*S. tymphimurium, E. coli*, etc.). Prophylaxis may be accomplished by administering the agent at a point where the subject is in or about to be in, a situation where endotoxin exposure may result. Classically, this occurs during surgery. Thus, a subject who is about to experience a surgical procedure may have the active ingredient administered preparatory to the procedure.

The effective amount of phospholipid and bile acid combination necessary for treatment of the subject can vary. In general, a dose up to from about 200 total mg to about 800 mg of phospholipid per kilogram of body weight of the subject is preferred, although the amount may drop, or increase, depending upon the severity of the endotoxemia or the degree of risk in the context of the prophylaxis. For cholanoic acids and salts, such as the bile acids and their salts, a dose of from about 10 mg to about 300 mg/kg of body weight, more preferably 15 mg to about 275 mg per kg of body weight is used.

It is desirable to administer the bile acid/bile acid salt and phospholipids in compositions which also contain neutral lipids, but this is not necessary, as neutral lipid free emulsions of phospholipids are also envisioned. The desirability of combined administration of the phospholipids results from the fact that the neutral lipids and phospholipids associate into particles which resemble the lipoproteins, but differ therefrom in that they contain no protein of peptide components, which are of course, always present in the lipoproteins.

Especially desirable forms of treatment are those where the phospholipid is a phosphatidylcholine, such as egg yolk phosphatidylcholine, soy based phosphatidylcholine or a sphingolipid. For the bile acid/bile acid salt, preferred are cholic acid and/or its salts, such as sodium cholate, sodium deoxycholate, and sodium chenodeoxycholate. With respect to the neutral lipids, it is preferred to use cholesterol ester or triglyceride, but other neutral lipids, such as squalene or other hydrocarbon oils, di- and mono-glycerides and antioxidants such as vitamin E may also be used.

The form in which the compositions may be administered can vary, with a bolus or other intravenous forms being especially preferred. When a bolus form is used, and the composition contains triglyceride, e.g., some care must be given in dosing. It is fairly well known that triglycerides are toxic if administered in too large an amount. The artisan of ordinary skill, however, can easily formulate the compositions so that the risk of triglyceride poisoning is reduced, or eliminated. In general, when a bolus form is used, the compositions should contain no more than about 80 weight percent by weight of triglyceride or other neutral lipid, preferably no more than 70 weight percent. Most preferably, the compositions should contain no more than about 50 weight percent, of neutral lipid, when a bolus is administered.

When non-bolus forms are employed, however, such as other intravenous forms, the risk of poisoning is decreased. Nonetheless, the ranges delineated supra are preferred for intravenous, or other forms of administration, although it must be understood that they are not required. Preferably, a dose of up to about 200 mg per kg of body weight of bile acid/bile acid salt or phospholipid is administered. Administration of up to about or even up to about 800 mg/kg is also feasible. Doses are general, however and will vary depending upon the subject and the form of administration.

As indicated, supra, the protein and peptide free formulations require that at least one phospholipid or bile acid/bile acid salt be present. For phospholipids, it is preferred that at least one neutral lipid, such as a triglyceride, diglyceride, or monoglyceride be present. The compositions may include additional materials such as sterols (e.g., cholesterol, β-sitosterol), esterified or unesterified lipids (e.g., cholesterol ester or unesterified cholesterol), hydrocarbon oils such as squalene, antioxidants such as vitamin E but these are not required. Of course, more than one phospholipid, and/or more than one neutral lipid may be used in any such formulation. When combinations of neutral lipid and phospholipid are used, the neutral lipid should be present at from about 3% up to about 50% by weight relative to the total amount of lipid in the composition.

In the case of the bile acid/bile acid salts, these may be used separately, or in combination a phospholipid, a neutral lipid, or both. With respect to these additional materials (e.g. phospholipids and neutral lipids), preferred species are those discussed and mentioned supra. Optional additional ingredients include those listed supra.

Also a part of the invention are compositions useful in treating endotoxemia. One embodiment of this feature of the invention is a composition containing at least one of each of a bile acid/bile acid salt, a phospholipid, and a neutral lipid, wherein the composition as a whole contains an endotoxemia alleviating amount of active ingredient. This composition preferably contains, by weight percent, from about 5% to about 30% by weight bile acid/bile acid salt, from about 3% to about 50% by weight neutral lipid, and from about 10% to about 95% by weight of phospholipid. Especially preferred are compositions containing from about 10–15% by weight of bile acid/bile acid salt, from about 5% to about 10% by weight of neutral lipid, and the balance of the composition being phospholipid.

It should be noted that these weight percentages are relative to compositions consisting of three components. When the three component system is combined with, e.g., a carrier, adjuvant, optional ingredients such as those discussed supra, the percentage by weight relative to the entire composition will drop. It is to be borne in mind that such therapeutic compositions are always protein free and peptide free.

In the case of compositions which do not contain a bile acid or a bile acid salt, such protein free, peptide free compositions contain, preferably, at least about 3% by weight of a neutral lipid, up to about 50% by weight neutral lipid, the balance being at least one phospholipid. Preferably, the neutral lipid is a triglyceride, but may be any of the additional neutral lipids discussed supra. Also, the phospholipid is preferably a phosphatidylcholine.

Other aspects of the invention will be clear to the skilled artisan and need not be reiterated here.

It will be understood that the specification and examples are illustrative but not limitative of the present invention and that other embodiments within the spirit and scope of the invention will suggest themselves to those skilled in the art.

We claim:

1. Protein and peptide free composition useful in treating endotoxemia, comprising:
   (a) neutral lipids in an amount ranging from about 3% to about 50% by weight total lipid in said composition, wherein at least a portion of said neutral lipids are triglycerides, and
   (b) at least one phospholipid.

2. The protein and peptide free composition of claim 1, wherein said neutral lipids further comprise at least one monoglyceride or at least one diglyceride.

3. The protein and peptide free composition of claim 1, wherein said phospholipid is a phosphatidylcholine.

4. The protein and peptide free composition of claim 1 wherein said neutral lipids further comprise cholesteryl ester.

5. The protein and peptide free composition of claim 1, further comprising sphingosine.

* * * * *

(12) EX PARTE REEXAMINATION CERTIFICATE (5740th)
United States Patent
Parker et al.

(10) Number: US 5,587,366 C1
(45) Certificate Issued: *Apr. 17, 2007

(54) COMPOSITIONS USEFUL IN PROPHYLAXIS AND THERAPY OF ENDOTOXIN RELATED CONDITIONS

(75) Inventors: Thomas S. Parker, Brooklyn, NY (US); Daniel M. Levine, New York, NY (US); Albert L. Rubin, Englewood, NJ (US); Bruce R. Gordon, New York, NY (US); Stuart D. Saal, New York, NY (US)

(73) Assignee: Sepsicure, L.L.C., Secaucus, NJ (US)

Reexamination Request:
No. 90/007,555, May 20, 2005

Reexamination Certificate for:
Patent No.: 5,587,366
Issued: Dec. 24, 1996
Appl. No.: 08/487,461
Filed: Jun. 7, 1995

( * ) Notice: This patent is subject to a terminal disclaimer.

Related U.S. Application Data

(63) Continuation-in-part of application No. 08/288,568, filed on Aug. 10, 1994, now Pat. No. 5,506,218, which is a continuation-in-part of application No. PCT/US93/07453, filed on Aug. 9, 1993, which is a continuation-in-part of application No. 07/928,930, filed on Aug. 12, 1992, now Pat. No. 5,344,822.

(51) Int. Cl.
*C07K 14/435* (2006.01)
*C07K 14/775* (2006.01)
*A61K 9/127* (2006.01)
*A61K 38/00* (2006.01)

(52) U.S. Cl. .................. 514/78; 514/171; 514/549; 514/552; 514/671

(58) Field of Classification Search ................. None
See application file for complete search history.

(56) References Cited

U.S. PATENT DOCUMENTS

| 4,115,313 A | 9/1978 | Lyon et al. |
|---|---|---|
| 4,314,997 A | 2/1982 | Shanbrom |
| 5,000,958 A | 3/1991 | Fountain et al. |
| 5,128,318 A | 7/1992 | Levine et al. |
| 5,578,583 A * | 11/1996 | Maranh ao .............. 514/49 |
| 5,652,339 A | 7/1997 | Lerch et al. |

FOREIGN PATENT DOCUMENTS

| DE | 25 56 592 A | 6/1977 |
|---|---|---|
| DE | 40 17 979 A1 | 12/1991 |
| DE | 43 10 935 A | 11/1993 |
| EP | 0 074 251 A | 3/1983 |
| EP | 0 391 369 A | 10/1990 |
| JP | 61 093 111 | 5/1986 |
| WO | WO-93/05797 | 4/1993 |

OTHER PUBLICATIONS

Kocsar, et al., "Effect of Bile Acids on the Intestinal Absorption of Endotoxins in Rats," J. Bact., 100:1, 220–223 (1969).
Schwartzenberg, et al., "Ursodeoxycholic Acid Modifies Gut-Derived Endotoxemia in Neonatal Rats," Ped. Res., 35:2, 214–217 (1994).
Anantharamaiah, "Synthetic Peptide Analogs of Apolipoproteins," Meth. in Enzymology, 128:627–647 (1986).

* cited by examiner

*Primary Examiner*—Evelyn Mei Huang

(57) ABSTRACT

Treatment and prophylaxis of endotoxin caused toxicity is disclosed. This is accomplished by administering phospholipid containing compositions to the subject. The compositions are protein and peptide free, and may contain trigylcerides, or other polar or neutral lipids.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1–5 are cancelled.

New claims 6–15 are added and determined to be patentable.

6. *A protein and peptide free composition useful in treating endotexmia, comprising:*
   *(a) trigylcerides in an amount ranging from about 3% to about 7% by weight of total lipid in said composition,*
   *(b) at least one monoglyceride or at least one diglyceride, and*
   *(c) phosphatidylcholine in an amount of at least 55% by weight of the total lipid in said composition.*

7. *The protein and peptide free composition according to claim 6, further comprising cholesteryl ester.*

8. *The protein and peptide free composition of claim 6, further comprising sphingosine.*

9. *A protein and peptide free composition useful in treating endotoxemia, comprising:*
   *(a) trigylcerides, in an amount ranging from 3% to about 7% by weight of total lipid in said composition,*
   *(b) at least one monoglyceride or at least one triglyceride, and*
   *(c) phosphatidylcholine in an amount of at least 55% by weight of the total lipid in said composition.*

10. *The protein and peptide free composition of claim 9, further comprising cholesteryl ester.*

11. *The protein and peptide free composition of claim 9, further comprising sphingosine.*

12. *A protein and peptide free composition useful in treating endotoxemia, comprising:*
    *(a) triglycerides in an amount ranging from 3% to 7% by weight of total lipid in said composition,*
    *(b) at least one monoglyceride or at least one diglyceride, and*
    *(c) at least one phospholipid.*

13. *The protein and peptide free composition of claim 12, wherein said phospholipid is a phosphatidylcholine.*

14. *The protein and peptide free composition of claim 12, further comprising cholesteryl ester.*

15. *The protein and peptide free composition of claim 12, further comprising sphingosine.*

\* \* \* \* \*